United States Patent
Armini et al.

[11] Patent Number: 5,980,974
[45] Date of Patent: Nov. 9, 1999

[54] COATED ORTHOPAEDIC IMPLANT COMPONENTS

[75] Inventors: Anthony J. Armini, Manchester; Stephen N. Bunker, Wakefield, both of Mass.

[73] Assignee: Implant Sciences Corporation, Wakefield, Mass.

[21] Appl. No.: 08/633,117

[22] Filed: Apr. 16, 1996

Related U.S. Application Data

[63] Continuation-in-part of application No. 08/589,018, Jan. 19, 1996, Pat. No. 5,674,293.

[51] Int. Cl.$^6$ .......................... C23C 14/04; C23C 14/06; A61F 2/36; A61F 2/30
[52] U.S. Cl. .................. 427/2.27; 427/526; 427/528; 427/529; 427/531; 427/527; 623/16; 623/18; 623/23
[58] Field of Search .................. 427/2.26, 2.27, 427/526, 527, 529, 528, 531; 623/16, 18, 23; 606/76

[56] References Cited

U.S. PATENT DOCUMENTS

| | | | |
|---|---|---|---|
| 4,021,326 | 5/1977 | Pollner et al. | 204/429 |
| 4,041,196 | 8/1977 | Baldi et al. | 427/252 |

(List continued on next page.)

FOREIGN PATENT DOCUMENTS

| | | | |
|---|---|---|---|
| 3027472 | 2/1982 | Germany | 427/2.27 |
| 3342562 | 6/1985 | Germany | 623/22 |

OTHER PUBLICATIONS

Dillich, S.A., et al. "Friction and Wear Behavior of a Cobalt–Based Alloy Implanted with Ti or N" *Mat. Res. Soc. Symp. Proc.* vol. 27, (1984) pp. 637–642. No Month.

Sioshansi, P., "Medical applications of Ion Beam Processes" *Nuclear Instruments and Methods in Physics Research* B19/20 (1987) 204–208. No Month.

Ogata, K., et al. "Properties of Aluminum Nitride Films by an Ion Beam and Vapor Deposition Method" *Nuclear Instruments and Methods in Physics Research* B39 (1989) 178–181. No month.

Kumar, P., et al. "Low wear rate of UHMWPE against zirconia ceramic (Y–PSZ) in comparison to alumina ceramic and SUS 316L alloy" *Journal of Biomedical Materials Research*, vol. 25 (1991) 813–828. No Month.

Iwaki, M., et al. "Surface modification of iron and steel by zirconium or yttrium ion implantation and their electrochemical properties" *Surface and Coatings technology*, 51 (1992) 1–5. No month.

(List continued on next page.)

*Primary Examiner*—Marianne Padgett
*Attorney, Agent, or Firm*—Foley, Hoag & Eliot LLP

[57] ABSTRACT

An improved coated orthopaedic implant component is disclosed. The implant may be coated with platinum, iridium or other metals for improved characteristics. Ion beam coating orthopaedic parts by ion implanting the parts with zirconium ions while the parts are immersed in an oxygen-containing background gas is also disclosed. The adhesion of the graded interface zirconium oxide surface layer so formed is further improved by the initial removal of surface contamination using an ion bombardment and the deposition of an intermediate layer of platinum or similar metal or silicon between the orthopaedic metal component and the zirconium oxide. Furnace heating results in atomic interdiffusion to enhance adhesion between the surfaces. The zirconium oxide provides a low friction, low wear articulating surface. The graded interface may be characterized by a blackish color and a transition between pure zirconium oxide and pure intermediate layer that extends over a thickness of hundreds of Angstroms. In an alternative embodiment, the thickness of the zirconium oxide coating may be increased by also adding a simultaneous deposition of zirconium oxide on the parts.

6 Claims, 6 Drawing Sheets

U.S. PATENT DOCUMENTS

| | | | |
|---|---|---|---|
| 4,137,370 | 1/1979 | Fujishiro et al. | 427/531 |
| 4,145,764 | 3/1979 | Suzuki et al. | 427/2.27 |
| 4,263,681 | 4/1981 | Notton | 606/76 X |
| 4,364,969 | 12/1982 | Dearnaley et al. | 427/531 |
| 4,427,501 | 1/1984 | Rogers | 205/176 |
| 4,433,005 | 2/1984 | Manty et al. | 427/531 |
| 4,599,085 | 7/1986 | Riess et al. | 623/16 |
| 4,615,705 | 10/1986 | Scales et al. | 623/11 |
| 4,634,600 | 1/1987 | Shimizu et al. | 427/531 |
| 4,693,760 | 8/1987 | Sioshansi | 427/531 |
| 4,729,905 | 3/1988 | Zhed et al. | 427/531 |
| 4,743,308 | 5/1988 | Sioshansi et al. | 204/192.31 |
| 4,743,493 | 5/1988 | Sioshansi et al. | 428/217 |
| 4,746,532 | 5/1988 | Suzuki et al. | 427/2.27 |
| 4,790,851 | 12/1988 | Suire et al. | 427/2.26 |
| 4,822,369 | 4/1989 | Oueveau et al. | 623/22 |
| 4,847,163 | 7/1989 | Shimanune et al. | 427/2.27 |
| 4,855,026 | 8/1989 | Sioshasi | 204/192.11 |
| 5,037,438 | 8/1991 | Davidson | 623/18 |
| 5,045,345 | 9/1991 | Singer | 623/18 |
| 5,123,924 | 6/1992 | Sionshansi | 623/16 |
| 5,133,757 | 7/1992 | Sionshansi | 623/16 |
| 5,205,921 | 4/1993 | Shirkanzadeh | 623/16 X |
| 5,314,475 | 5/1994 | Repenning | 427/2.27 |
| 5,362,311 | 11/1994 | Amino | 623/22 |
| 5,383,934 | 1/1995 | Armini et al. | 623/16 |
| 5,593,719 | 1/1997 | Dearnaley et al. | 427/528 |
| 5,618,575 | 4/1997 | Peter | 427/529 |

OTHER PUBLICATIONS

Williams, J.M. et al., "Ion Implantation of Surgical Ti–6Al–4V Alloy," "Surface Modification of Metals by Ion Beams," Proceedings of the International Conference on Surface Modification of Metals by Ion Beams, pp. 237–246 (Sep. 1984).

R. Sizman, "The Effect of Radiation Upon Diffusion in Metals," *Journal of Nuclear Materials* 69 & 70, pp. 386–412 (1968). No. Month.

Streicher, R.M., et al. Ceramic Surfaces as Wear Partners for Polyethylene, *Bioceramics,* vol. 4, (Sep. 1991).

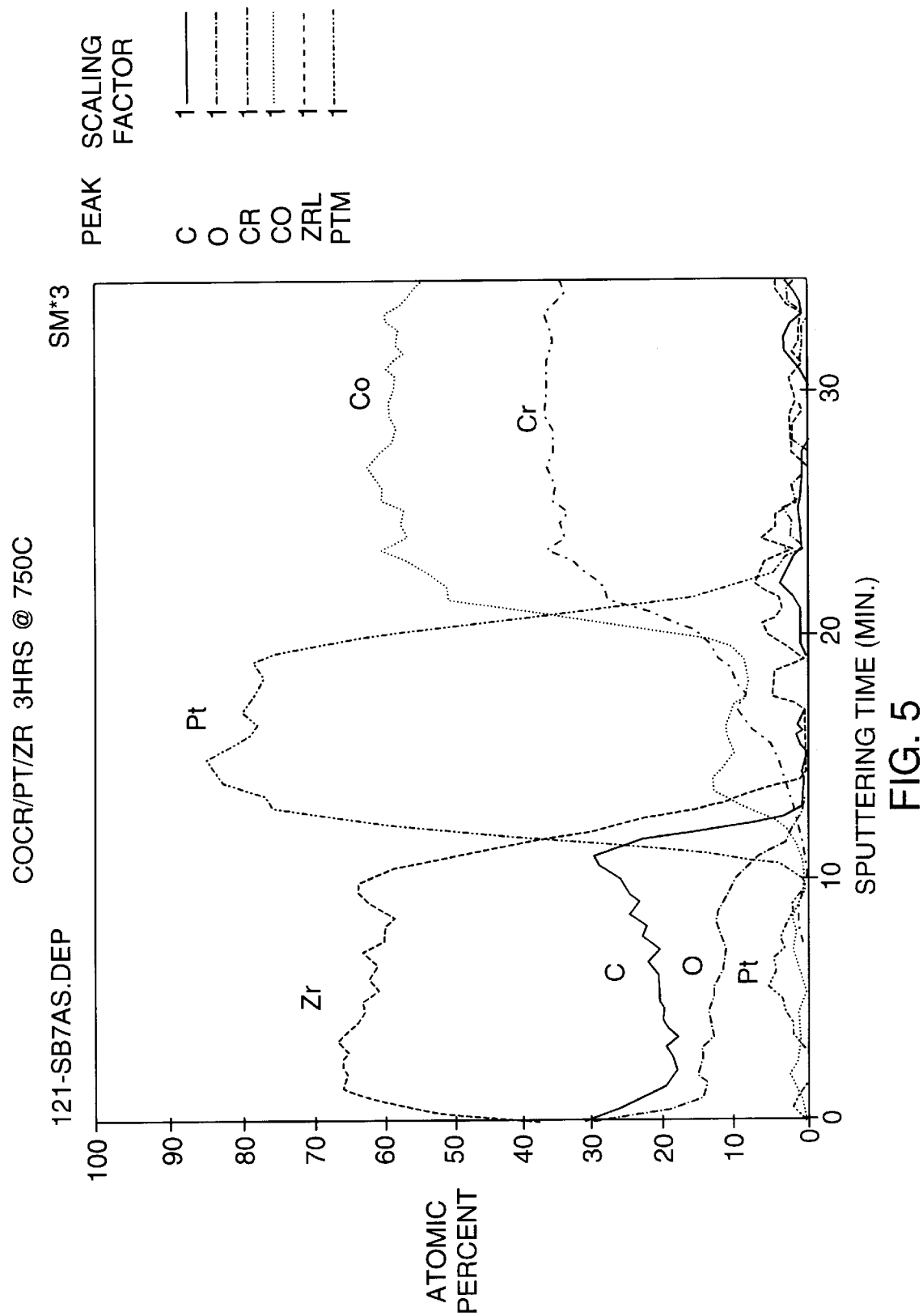

2

COATED ORTHOPAEDIC IMPLANT COMPONENTS

This application is a continuation-in-part of U.S. patent application Ser. No. 08/589,018 filed Jan. 19, 1996, now U.S. Pat. No. 5,674,293.

TECHNICAL FIELD

The present invention relates to improved coating of orthopaedic implant components.

BACKGROUND OF THE INVENTION

It is known that coating of the metal articulating surface of orthopaedic devices can improve wear and decrease friction, and improve other surface properties, in implantable orthopaedic devices. For example, it is possible to improve these properties by replacing the metal surface with a continuous surface layer consisting of a ceramic material. Zirconium oxide ($ZrO_2$ or zirconium oxide) has been found to be beneficial. This is described in U.S. Pat. No. 5,037,438, J. Davidson et al and also in an article titled "Low Wear Rate of UHMWPE Against Zirconium oxide Ceramic (Y-PSZ) in Comparison to Alumina Ceramic and SS316L Alloy", found in the J. of Biomed. Mat. Res. 25, p. 813 (1991).

In the method of growing a zirconium oxide coating on orthopaedic devices described in U.S. Pat. No. 5,037,438, the zirconium oxide is formed by diffusing oxygen gas into the metal at a high temperature in a furnace for a suitable period of time. The process occurs at atmospheric pressure and results in the chemical reaction of the zirconium metal workpiece and oxygen to form a surface layer of zirconium oxide. This method, however, requires that the prothesis be fabricated from pure zirconium metal, which may not be suitable for implantation into humans.

One well-known alternative is the use of ion implantation of various elements of the implant component for improving the wear, friction, and other surface properties of many metal alloys. See "Surface Modification of Metals by Ion Beams", Elsevir Sequoia (1984). For alloys containing primarily the elements cobalt and chromium, both ion implanted nitrogen and titanium have been shown to improve friction and wear properties. See "Friction and Wear Behavior of Cobalt-Based Alloy Implanted with Ti or N", Mat. Res. Soc. Symp. Proc. 27, p. 637 (1984). For orthopaedic surgical implants, cobalt-chrome alloy implanted with nitrogen has been found to improve the corrosion and subsequent wear/friction properties of the prosthetic joint. See "Medical Applications of Ion Beam Processes", Nuc. Inst. and Meth. in Physics Res. B19/20., pg. 204–208 (1987). Further, the idea of using an ion beam and physical vapor deposition simultaneously bombarding a metal surface has been in use for flat substrates. See "Properties of Aluminum Nitride Films by an Ion Beam and Vapor Deposition Method", Nucl. Inst. and Meth. in Phys. Res. B39, p. 178 (1989).

Ion implantation of nitrogen does produce some improvement in the wear and friction properties of those alloys containing predominantly cobalt and chromium when rubbing against ultra-high molecular weight polyethylene (UHMWPE) in a laboratory test, such as a pin-on-disk wear test. See U.S. Pat. No. 5,123,924, Sioshansi et al.

Zirconium ions have been ion implanted into iron and steel to improve the corrosion properties. See "Surface Modification of Iron and Steel by Zirconium or Yttrium Ion Implantation and Their Electrochemical Properties", from "Surface Modification of Metals by Ion Beams 7", Eds. F. A. Smidt, G. K. Hubler, and B. D. Sartwell, Elsevier Sequoia S. A., p. 1 (1992).

SUMMARY OF THE INVENTION

It is therefore an object of this invention to provide improved coating of orthopaedic prostheses and to provide improved orthopaedic prostheses with a coating on the articulating surface.

It is a further object of this invention to provide a method for ion-coating the articulating surface of femoral hip ball and knee orthopaedic prostheses made from either an alloy primarily consisting of cobalt and chromium or an alloy primarily consisting of titanium or stainless steel alloys.

It is a further object of this invention to provide such a method for creating orthopaedic prostheses having a longer useful life by reducing polyethylene wear debris.

It is a further object of this invention to improve the adhesion between the zirconium oxide ion coating and the said femoral component to decrease the possibility of coating delamination or failure.

According to the present invention, a coating of platinum group materials may be provided on the implant parts. The parts thus coated are found to have improved surface characteristics such as wear.

In another embodiment of the invention, the implant parts are coated with a platinum group material or silicon and with zirconium oxide. This may be achieved by using a conventional method for coating the parts with the platinum group material or silicon and by implanting zirconium into the parts in the presence of oxygen, according to U.S. Pat. No. 5,383,934, having common inventors and assigned to a common owner.

BRIEF DESCRIPTION OF DRAWINGS

Other objects, features and advantages will occur to those skilled in the art from the following description of a preferred embodiment and the accompanying drawings in which:

FIG. 5 illustrates a depth profile of a flat disk, demonstrating interdiffusion.

DETAILED DESCRIPTION OF THE PREFERRED EMBODIMENTS

While the description of the preferred embodiment relates to coating of an implant component that is made of an alloy composed primarily of cobalt and chromium, such as either case ASTM-F75 alloy or wrought ASTM-F799 alloy, the component may also be a surgical alloy composed primarily of titanium, such as titanium-6aluminum-4vanadium. The component may also be made of a surgical grade of stainless steel. The component is preferably a femoral hip ball or femoral knee component.

Ion implantation of zirconium ions into orthopaedic prostheses that are immersed in a low pressure, oxygen-containing gas will result in the addition of zirconium atoms to the workpiece together with a concurrent chemical reaction with oxygen to form a low-friction surface layer of zirconium oxide. A method of forming a highly adherent surface layer of zirconium dioxide on a cobalt-chrome alloy substrate was disclosed in U.S. Pat. No. 5,383,934, which is fully incorporated herein by reference. This patent discloses ion implanting parts of implant components with zirconium ions in the presence of an oxygen-containing background gas. The implanted zirconium reacts with the oxygen to form zirconium-oxide.

Zirconium metal and zirconium oxide do not, however, inherently tend to bind to alloys substantially consisting of cobalt and chromium (cobalt-chrome or cobalt-chromium alloy). This is a consequence of the low mutual solubility and low chemical reactivity between zirconium and cobalt or chromium. In the method disclosed in U.S. Pat. No. 5,383,934, this deficiency is partially addressed by using the ion implantation technique to deposit atoms of the zirconium oxide coating below the surface of the cobalt-chrome prosthesis. This is described as a graded or blended interface, which avoids the abrupt transition in material properties typical of a coating that is deposited solely on the external surface by such common techniques as evaporation, sputtering or electron arc discharge.

One alternative is to use a platinum group material for coating part of an implant component, which bonds well with metal implants. As used in this specification, including the claims herein, the term "platinum group material" refers to platinum, iridium, ruthenium, rhodium and palladium, as well as alloys thereof. In the preferred embodiment, the implant parts are coated with substantially pure platinum, substantially pure iridium, or a platinum—10% iridium alloy.

Figure 1A:
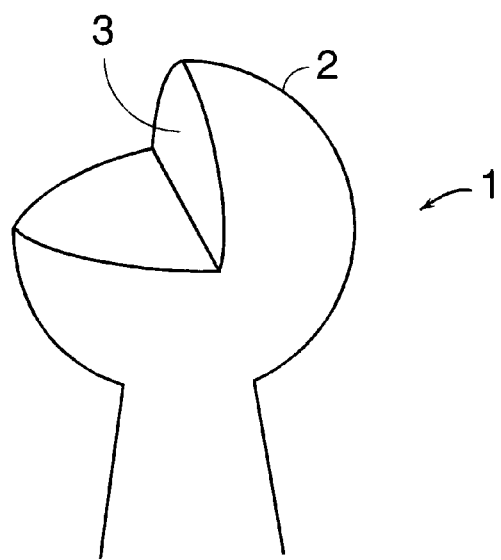
FIG. 1A illustrates part of an implant component coated with a platinum group material according to the present invention.

FIG. 1A illustrates a part of an implant component 1 that has been coated according to one embodiment of the present invention. In this embodiment, the implant component 1 is made of a cobalt-chrome alloy 3 and is coated with a thin layer of a platinum group material 2.

The coating of a thin layer of a platinum group material on the component can be performed by any of several well-known processes, such as evaporation, sputtering, or arc discharge. The surface of the prosthesis should be pre-cleaned of impurities or oxides using accelerated ion bombardment, a well-known coating process step.

Figure 2:
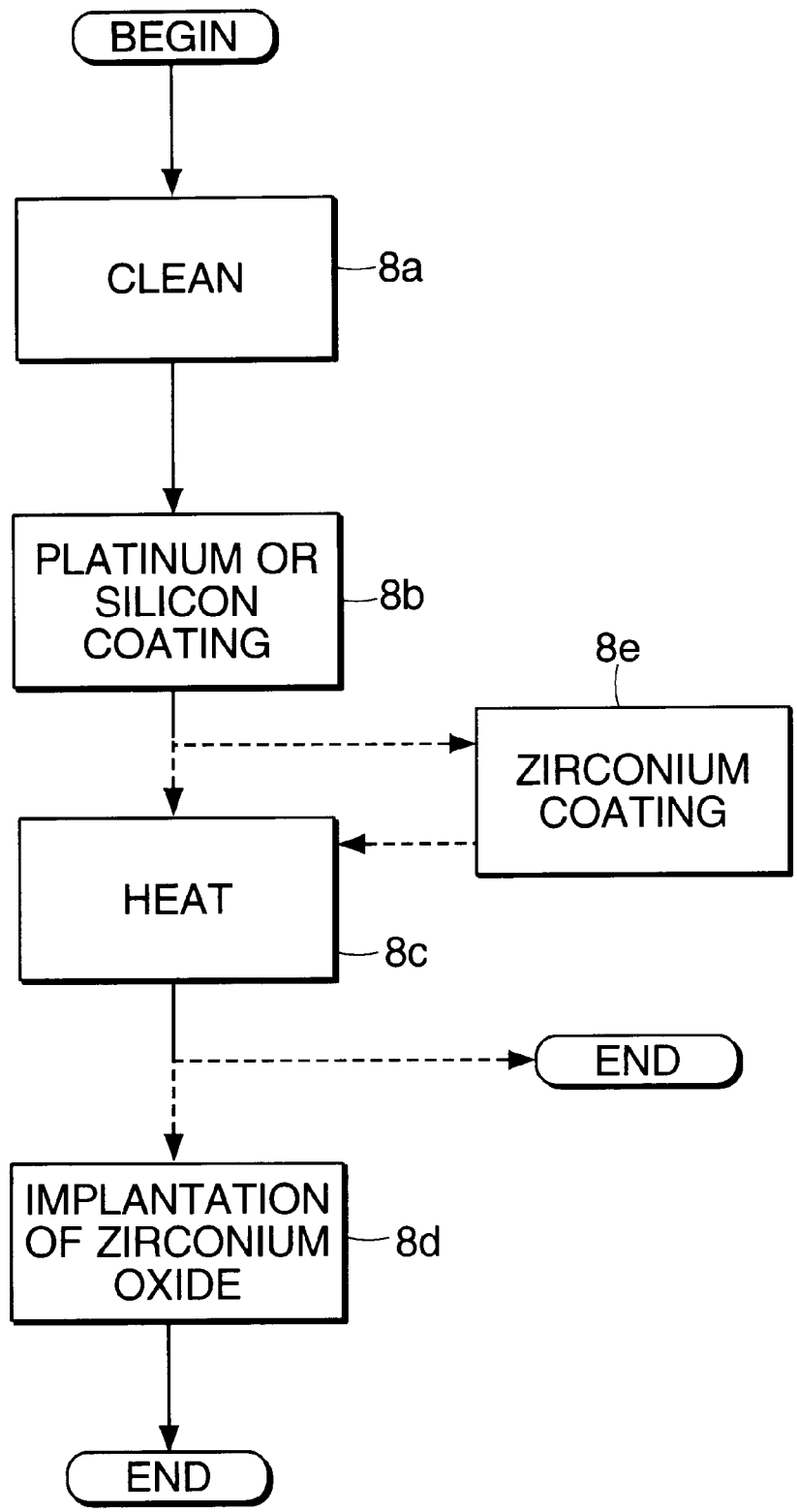
FIG. 2 illustrates the coating process of a preferred embodiment of the present invention.

FIG. 2 illustrates the preferred method for coating parts of the implant component 1. While the process is described in terms of the preferred embodiment, one of skill in the art would understand that various modifications in the process and the operating parameters for the process could be made, and are within the scope of the invention. The process begins at step 8a of cleaning the part, by bombarding the component with accelerated ions to remove contamination and oxides. Any convenient ion species may be used for this step. A commonly used technique is glow discharge with argon ions. The step 8a is followed by a step 8b of depositing a thin layer of a platinum group material by any of several common coating technologies, such as evaporation, sputtering or arc discharge. In the preferred embodiment, the step 8b is performed by sputtering achieved by bombarding a plate made of the platinum group material with two keV argon ions preferably using a commercially available magnetron sputtering apparatus, for example, one available from AJA International, North Scituate, Mass. The coated prosthesis is then heated at a step 8c in an oxygen-free furnace which may be provided either by vacuum or an inert gas atmosphere, such as argon. The heat is preferably between 100° C. and 1000° C. and lasts for at least ten minutes. In a preferred embodiment, the heating is for a period of one to three hours at 750° C. The residual oxygen can be as high as $1 \times 10^{-3}$ Torr for platinum. This heating results in interdiffusion of the atomic species of the coating and the implant component. For a preferred embodiment, processing is complete following the step 8c.

The platinum group material coating is preferably 0.2 to 5 microns in thickness over the articulating surface. In a preferred embodiment, the coating is about 1 micron thick.

Figure 1B:
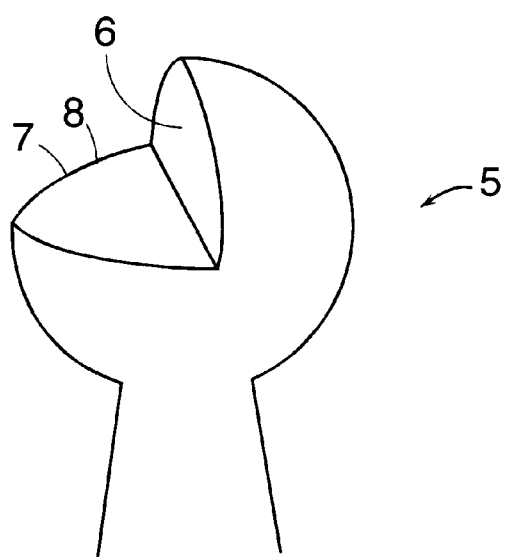
FIG. 1B illustrates part of an implant component coated with a platinum group material or silicon and zirconium oxide according to the present invention.

FIG. 1B illustrates an alternative embodiment of the present invention. FIG. 1B shows a part of an implant component 5 made of cobalt-chrome 6 and having both a platinum group material or silicon coating including a zirconium graded interface layer 7 and an external zirconium oxide coating 8. The use of a metal coating combined with a zirconium oxide coating may be desirable because the mutual solubility or chemical reactivity between zirconium and zirconium oxide with materials other than cobalt-chrome can be relatively high, thus permitting better adhesion with the zirconium oxide than with simple zirconium oxide coating or even a graded zirconium oxide interface alone. Such an intermediate material requires a common mutual solubility with both the metal of the implant component, such as a cobalt-chrome, and zirconium. Platinum group materials are acceptable intermediate materials since cobalt and chromium are highly soluble in platinum group materials. See ASM Handbook #3 for solubility diagrams. Zirconium has a greater solubility in platinum group materials than in cobalt or chromium. Silicon is also an acceptable material. Silicon chemically reacts with cobalt and chromium to form metal suicides. Zirconium also reacts with silicon to form a silicide. Adhesion is greatly improved by mutually diffusing the materials together at elevated temperature in an oxygen-free environment.

Thus, as explained in greater detail below, the component may be treated by coating the articulating surface with a platinum group material or silicon as an adhesion coating and by zirconium oxide achieved through ion implantation of zirconium in the presence of oxygen.

For ion implantation of zirconium, it is known to deposit the zirconium atoms at some depth below the surface of the workpiece. Oxygen or oxygen-containing molecules will diffuse into the workpiece during the ion bombardment. The oxygen molecules react chemically with the ion implanted zirconium atoms to form an oxide. This process may be accelerated by the energy provided by the bombarding ions. The zirconium oxide molecules gradually increase in number with dose and eventually merge into a continuous layer at or above a preferred dose depending on ion energy and angle of incidence. High energy ion bombardment of surfaces also results in the loss of surface atoms by a process called sputtering. Sputtering removes both workpiece atoms and some of the ion implanted zirconium atoms such that it is not always possible to achieve a high enough concentration of zirconium to form pure zirconium oxide. A thin layer of nearly pure zirconium oxide will often form only when the angle of incidence of the zirconium ion beam is nearly normal to the surface, because this condition results in the lowest rate of sputtering.

The ion implantation process does not deposit every implanted atom at precisely the same depth. A range of depths inevitably occurs. This is beneficial for creating a graded or blended interface between the platinum group material or silicon intermediate layer and zirconium oxide surface coating which is not atomically abrupt but gradually varies in composition over a range of depths. Such a graded interface preferably varies smoothly between the composition of the pure workpiece material and nearly pure zirconium oxide at the surface and permits the physical properties between the two materials to change gradually over a range of depths. Such a graded or blended interface is beneficial for providing improved adhesion compared to conventional coatings, which are simply laid on the surface of the workpiece and which may more easily delaminate at the interface.

Referring again to FIG. 2, the process for coating component 5 is described. While the process is described in terms of the preferred embodiment, one of skill in the art would understand that various modifications in the process and the operating parameters for the process could be made, and are within the scope of the invention. The process may begin at the step 8a of cleaning the part, by bombarding the component with accelerated ions to remove contamination and oxides. Any convenient ion species may be used for the step 8a. A commonly used technique is glow discharge with argon ions. The process continues by the step 8b of depositing a thin layer of the platinum group material or silicon by any of several common coating technologies, such as evaporation, sputtering or arc discharge. In one embodiment, the coating of the platinum group material or silicon is about 0.1 to 1 microns in thickness. In a preferred embodiment, the coating is 0.5 micron in thickness.

Optionally, the step 8e of coating the articulating surface of the piece with a layer of zirconium is performed. In a preferred embodiment, the layer is about 0.2 micron in thickness. This also may be done by magnetron sputtering.

Following the step 8b, or in one embodiment step 8e, is the step 8c where the coated prosthesis is heated in an oxygen-free furnace which may be provided either by vacuum or an inert gas atmosphere, such as argon. The heating is preferably for a period of one to three hours at 750° C. The residual oxygen can be as high as $1\times10^{-3}$ Torr for platinum group materials and $1\times10^{-5}$ Torr for silicon. This heating results in interdiffusion of the atomic species of the coating and prosthesis.

Following the step 8c is a step 8d where the component is exposed to a zirconium ion beam in an oxygen-containing gas, such gases typically including at least one of oxygen, ozone, water vapor, or hydrogen peroxide, and providing an ion beam consisting primarily of zirconium ions to the immersed component to form an implanted zirconium oxide layer in the component. The partial pressure of the oxygen-containing gas or gases should be in the range from $5\times10^{-6}$ Torr to $1\times10^{-3}$ Torr and preferably at $4\times10^{-5}$ Torr. The oxygen-containing gas may be composed of any one or more of the compounds of pure oxygen, water vapor, ozone, or hydrogen peroxide. Other gases, such as nitrogen, may also be present and which do not contribute to the formation of the oxide. The oxygen-containing gas is preferably oxygen.

The process may further include providing simultaneously a source of zirconium, which may include zirconium or zirconium oxide. This can be done using any of a variety of conventional techniques. A flux of zirconium may be supplied by evaporation using an electron beam evaporator. In a preferred embodiment, the ion beam and the flux of zirconium treat similar surface regions of the immersed component during each complete cycle of movement of the component relative to the ion beam.

The zirconium ion beam preferably has an energy of between 20 keV and 400 keV. The zirconium ion beam preferably delivers a total ion dose of between $5\times10^{16}$ and $5\times10^{18}$ ions/cm$^2$. Preferably, for a flat surface whose normal axis coincides with the direction of the ion beam, the dose is $3\times10^{17}$ atoms/cm$^2$ for a 150 keV zirconium ion beam. Curved or tilted surfaces may require other preferred doses, depending on the geometry. An appropriate dose will convert a layer to substantially all zirconium oxide, and can be determined by one of ordinary skill in the art via routine experimentation.

The process may further include maintaining the immersed component equilibrium temperature in the ion beam at a temperature between 25° C. to 600° C., which may be accomplished by adjusting the cooling to the fixture to which the component is mounted during treatment. A preferred temperature is 250° C.

The process may further include simultaneously moving the component relative to the ion beam about two transverse axes during implantation to create a more uniform implanted layer. The ion beam may be provided at an angle to the component. During the formation of the graded zirconium oxide interface layer, the process may further include selection of the deposition rate per unit area for the zirconium oxide surface coating which closely equals the rate of loss caused by zirconium ion beam sputtering. For an immersed component which exhibits different average sputtering rates for different regions of its surface, the relative flux per unit area is preferably first selected to form an ion implanted zirconium oxide graded interface layer in a region of lowest average sputtering followed sequentially by selection of relative flux for regions of higher average sputtering.

The implanted zirconium oxide graded layer is preferably from 50 to 5000 Angstroms thick.

Many useful components have curved or tilted surfaces that cannot form a nearly pure ion implanted buried layer of zirconium oxide because of a high rate of sputtering by the ion beam due to the angle of incidence of the beam at the surface. This limitation may be overcome by additionally providing a source of zirconium or zirconium oxide which deposits a coating on the workpiece at a rate which closely equals the rate of loss of atoms caused by sputtering. The flux of zirconium may be provided by known methods such as high temperature evaporation, sputtering, or electron arc discharged. This coating may be removed by sputtering as rapidly as it is deposited, providing no substantial net gain or loss of either the coating or workpiece materials. Such a coating rate allows atoms of the zirconium ion beam to be nearly completely retained below the surface of the workpiece without losses caused by sputtering. The concentration of ion implanted zirconium atoms below the surface can then be increased to a preferred level by selecting a dose which makes a zirconium oxide graded interface layer. A preferred rate of coating deposition depends on geometry of the work piece and may be determined visually by a blackening of the surface after a sufficient zirconium ion dose is provided to form the zirconium oxide graded interface layer. An insufficient coating rate during the ion implantation of zirconium causes a silver-grey color on a polished surface, and an excessive rate causes a colored hue, such as red or green, which is characteristic of a reflection optical interference effect.

Figure 3:
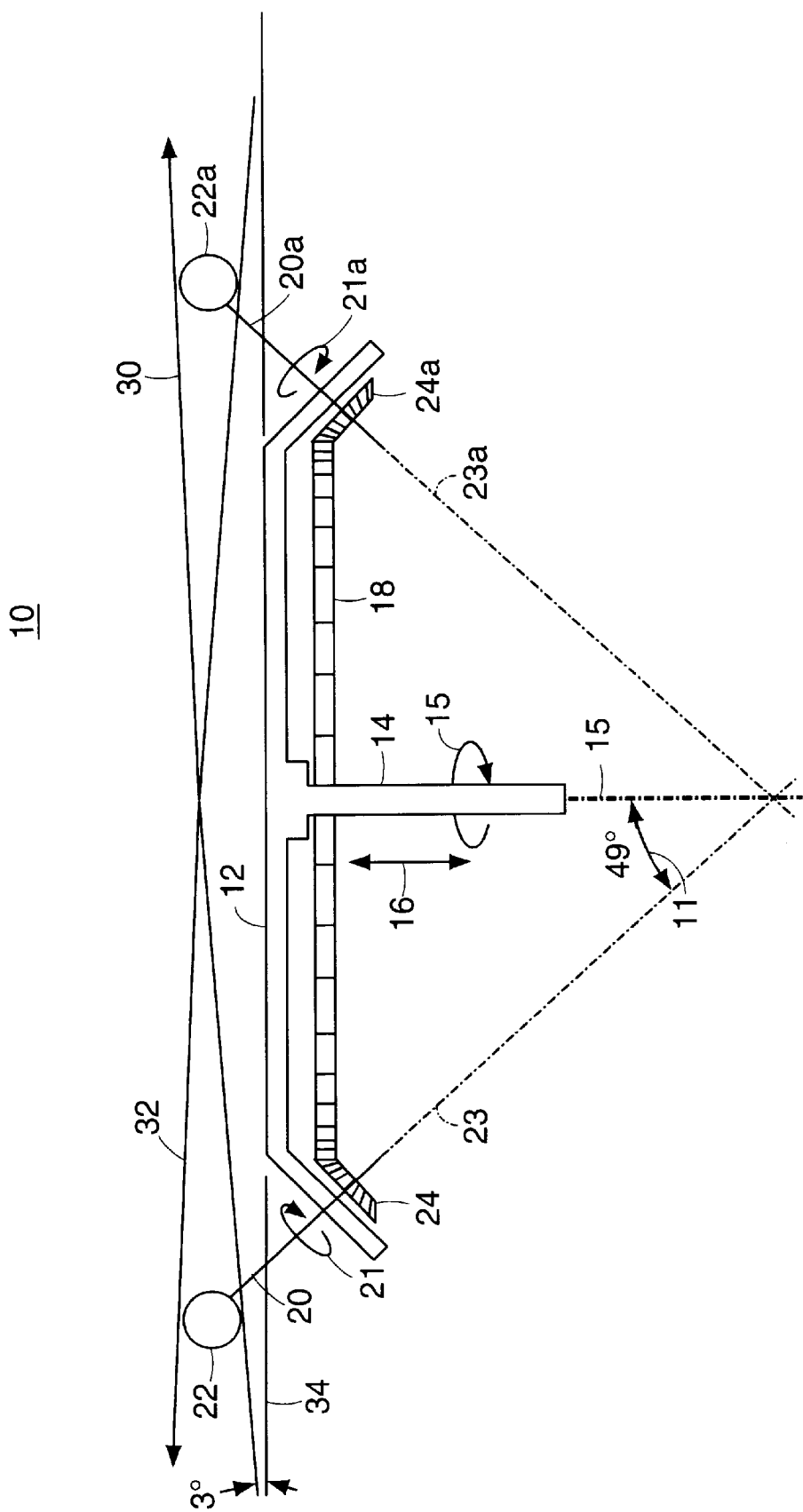
FIG. 3 is a schematic diagram of an ion implantation apparatus for accomplishing the method of this invention.

There is shown schematically in FIG. 3 ion implantation apparatus 10 for extremely uniformly ion beam implanting or coating irregularly-shaped parts. Apparatus 10 includes rotatable turntable or fixture 12 fixed to rotatable shaft 14.

Below turntable 12 there is a fixed disc 18 having a gear-engaging surface to act as a fixed sun gear. Parts 22, 22a to be coated, for example prosthetic hip balls, are mounted on shafts 20, 20a, respectively, to which are fixed planetary gears 24, 24a, that are engaged with the gear engaging surface of sun gear 18. When shaft 14 is rotated in the direction of arrow 15, balls 22 are caused to rotate around axis 15 as well as shaft axis 23, 23a to simultaneously rotate parts 22, 22a about two transverse axes. Preferably the angle between axis 15 and axis 23 is acute, and an angle of 49° has been found to result in extremely uniform ion treating of the surfaces of parts 22, 22a.

While the parts are rotating, they are exposed to one or more ion beams 30 and 32 that are preferably provided at a slight angle to plan 34 of fixture 12 so that the parts do not shadow each other. For implantation of prosthetic hip ball components, the beam axis is preferably approximately 3° to 10° from plane 34. The important parameter is the prevention of shadowing of the part by another. The beam angle necessary to accomplish this may be determined by drawing a line from the bottom of part 22 to the top of part 22a and determining the angle at which that line intersects plan 34. When the beam is provided at least this angle, the part closest to the beam source will not shadow the rear part.

Figure 4A:
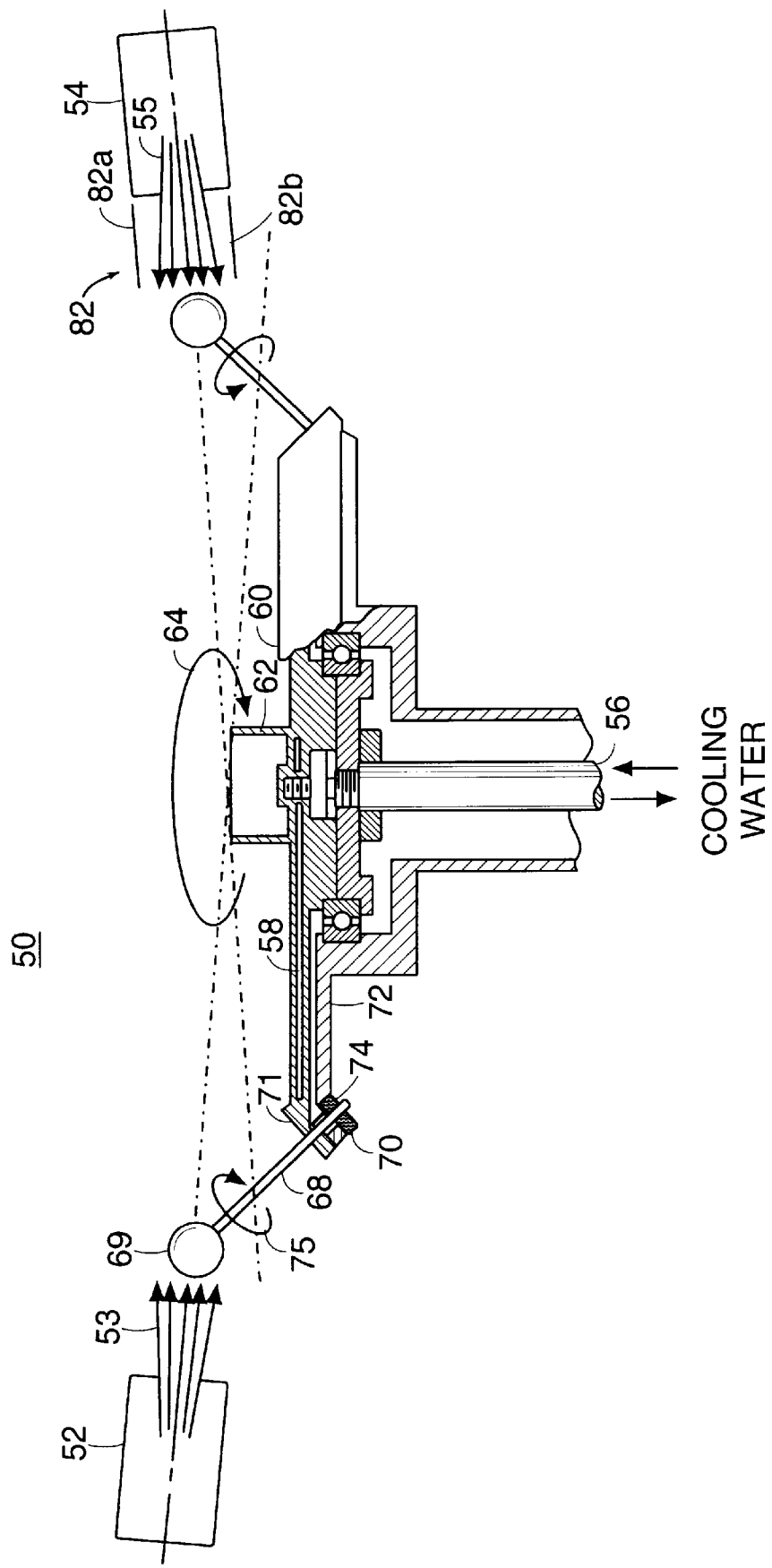
FIG. 4A is a detailed, partly cross-sectional view of a preferred embodiment of the apparatus of FIG. 3.

Apparatus 50, FIG. 4A, has been successfully used for uniformly ion-beam coating prosthetic hip balls with zirconium ions on cobalt chromium alloy prostheses. Preferably, the balls are spaced as closely as possible together so that ion beam is not wasted.

Beams 53, 55, FIG. 4A, are typically approximately one inch in diameter and are preferably scanned in relation to the parts being coated by either translating fixture 60 in the direction of arrow 16, FIG. 3, or electrostatically deflecting the beams for example by using deflection mechanism 82, FIG. 4A, including plates 82a, 82b for applying a voltage gradient across the beam. Preferably, the part-holding fixture is continuously translated up and down a distance approximately equal to the height of the parts being coated to insure that the beams are uniformly scanned across the surfaces being coated.

The ion beam dose may be chosen as desired, and is preferably between about $5 \times 10^{16}$ and $5 \times 10^{18}$ ions/cm$^2$. The ion beam current density is defined as the ion beam current divided by the cross-sectional area whose normal axis is parallel to that of the direction of the ion beam. The ion beam current density is typically chosen to be between approximately 200 to 2,000 microamperes/cm$^2$ with a beam energy between about 20 keV and 400 keV. The ion beam current density is chosen as high as possible consistent with the ion beam generation equipment used so as to provide a high speed economically viable process. The total ion beam power is defined as the ion beam current times the accelerating voltage applied to the beam. The total ion beam power divided by the total area swept out by the array of workpieces defines the ion beam power dissipation density. The ion beam power dissipation density is selected to maintain the workpieces at an average temperature between 50° C. to 600° C. during processing.

Figure 4B:
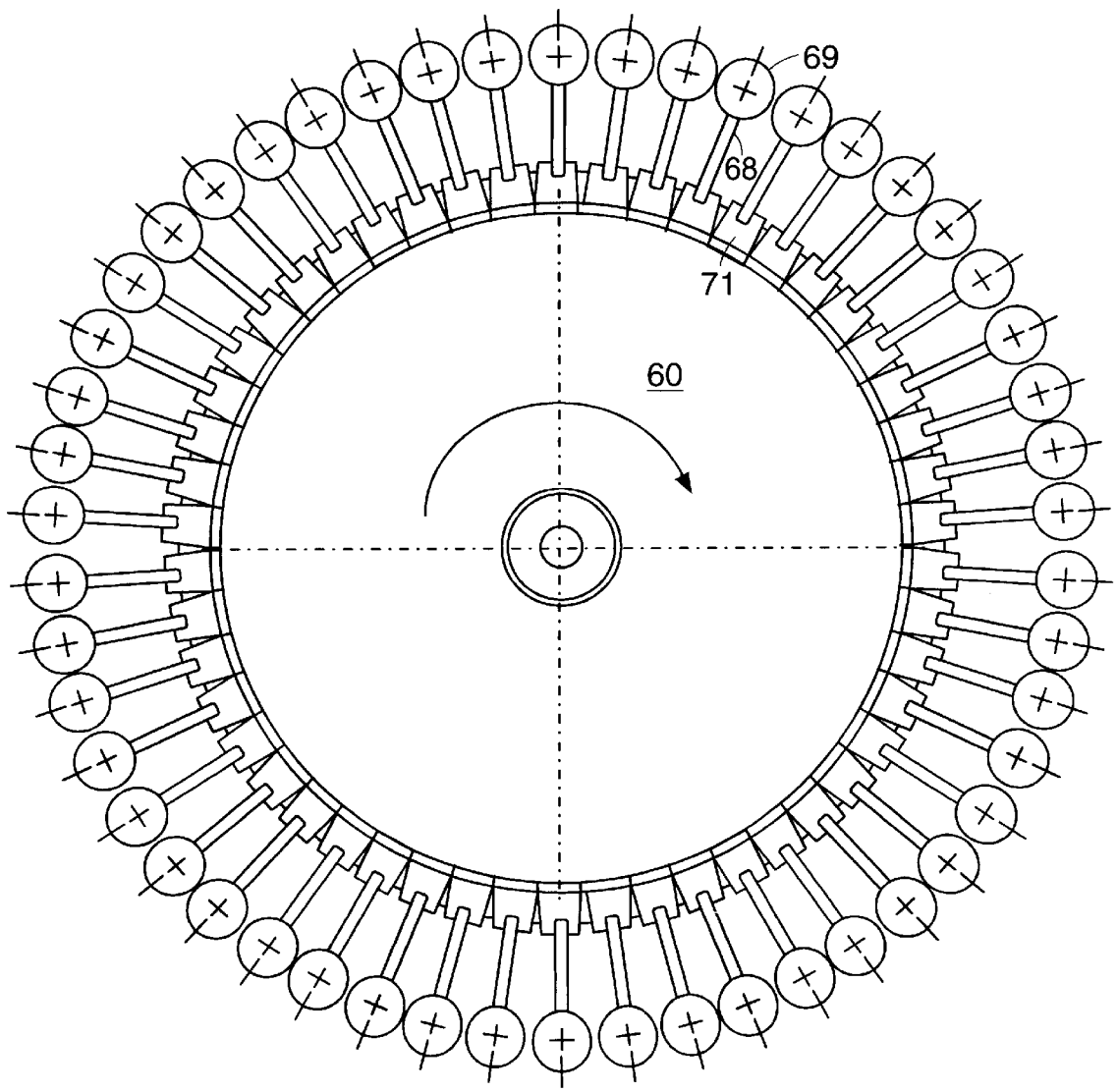
FIG. 4B is a top view of the device of FIG. 4A illustrating the close packing of the parts being coated.

A spherical workpiece, such as a femoral hip prosthesis, can be ion beam implanted with a graded interface of zirconium oxide using the apparatus of FIGS. 4A and 4B. It is realized that with said apparatus, only a limited area on a spherical workpiece can be ion beam treated to produce a graded interface of ion implanted zirconium oxide when a fixed flux per unit area of zirconium oxide coating deposition and a fixed flux per unit area of zirconium ion beam is applied. It is further realized that such a limited area consists of those regions on the spherical workpiece subjected to a similar average rate of sputtering as the spherical workpiece is manipulated to present all of its articulating surface to the zirconium ion beam and coating deposition. It is further realized that once a blackish graded interface zirconium oxide layer has formed, an increase in the coating deposition flux per unit area relative to the zirconium ion beam flux per unit area will deposit a zirconium oxide coating over the blackish graded interface zirconium oxide layer.

Therefore, an ion implanted graded interface zirconium oxide layer can be introduced into a spherical workpiece by simultaneously subjecting the surface to a zirconium oxide coating deposition flux per unit area and a zirconium ion beam flux per unit area while immersed in a partial pressure of oxygen. The total dose of zirconium ions and the fluxes per unit area are first selected to form a blackish graded interface layer in a region on the workpiece which is subjected to the lowest average rate of sputtering. If the apparatus of FIGS. 4A and 4B is employed, this region will be on the rotation axis of the spherical workpiece. After the first region is so treated, the coating deposition flux per unit area relative to the zirconium ion beam is incrementally increased to form the blackish graded interface layer in a region subjected to a higher average rate of sputtering. This process is repeated until all the desired surface regions are so treated. On a spherical workpiece a coating of zirconium oxide will accumulate on those regions that have smaller average rates of sputtering than the region currently being treated to form the blackish graded interface layer of ion implanted zirconium oxide.

It is realized that the method of forming a blackish ion implanted layer of zirconium oxide described for spherical orthopaedic workpieces may also be applied as a general method for other shapes of orthopaedic workpieces, such as femoral knee prostheses. It is further realized that other shapes of orthopaedic workpieces may require a different type of apparatus for manipulating the workpiece to ensure uniform treatment than the type shown in FIGS. 4A and 4B.

A preferred embodiment for ion treating a CoCr spherical femoral hip prosthesis component includes the steps of coating the articulating surface with about 0.5 micron thickness of platinum as described above, depositing about a 0.2 micron thickness of zirconium on the platinum coating, heating the component at 750° C. for about three hours in a high vacuum ($1 \times 10^{-6}$ Torr), and implanting zirconia under the following process (a) Blending Phase

| | |
|---|---|
| Ion Beam: | Zirconium 90 |
| Beam Current: | 0.5 mA |
| Beam Energy: | 190 keV |
| Scanned Area: | 58 cm$^2$ |
| Evaporant: | Zirconium |
| Deposition Rate: | 0.4 to 10Å/sec in 3 steps (determined to balance sputter rate) |
| Oxygen Pressure: | $3 \times 10^{-5}$ Torr |
| Dose at Each Step: | $2 \times 10^{17}$ Zr$^+$/cm$^2$ |
| Rotational Axis of Prosthesis: | 45° to axis of ion beam and evaporator |

(b) Growth Phase

| | |
|---|---|
| Ion Beam: | Zirconium 90 |
| Beam Current: | 200 μA (constant) |
| Beam Energy: | 36 keV (constant) |
| Scanned Area: | 58 cm$^2$ |
| Evaporant: | Zirconium |

-continued

| Deposition Rate: | 1.40Å/sec. (constant) |
| --- | --- |
| Oxygen Pressure: | $3 \times 10^{-5}$ Torr |
| Time Duration: | 2 Hours |

A test was performed to measure intermixing of the platinum and zirconium layers on a cobalt-chrome alloy, without ion implantation of zirconium into the workpiece. A flat CoCr alloy disk specimen was first coated with 2000 Angstrom of platinum and then coated with 3000 Angstrom of zirconium using ion beam sputtering. The specimen was then heated in a vacuum furnace for 3 hours at 750° C.

FIG. 5 shows a depth profile of the surface of the sample using Auger electron spectroscopy. As can be seen, the platinum coating has been penetrated on the left side with zirconium and on the right side by both the cobalt and chromium of the substrate alloy. The specimen processed by the above process now has enhanced adhesion between the zirconium outer coating and the CoCr substrate through the use of the intermediate platinum layer.

Although specific features of the invention are shown in some drawings and not others, this is for convenience only as some feature may be combined with any or all of the other features in accordance with the invention. While the invention has been disclosed in connection with the preferred embodiments shown and described in detail, various modifications and improvements thereon will become readily apparent to those skilled in the art. Accordingly, the spirit and scope of the present invention is to be limited only by the following claims.

What is claimed is:

1. A process for treating an articulating surface of a metallic femoral component of an orthopaedic implant, comprising steps of:

(a) depositing on the articulating surface of the component an adhesion coating of a platinum group metal selected from the group consisting of platinum, iridium, ruthenium, rhodium, palladium and alloys thereof;

(b) heating the component under conditions sufficient to cause atomic interdiffusion of the adhesion coating into the metallic component thereby forming a first graded interface between the articulating surface and the adhesion coating;

(c) immersing the component in an oxygen-containing gas; and (d) exposing the immersed component to an ion beam of zirconium under conditions sufficient to form a zirconium oxide coating on said adhesion coating.

2. The process of claim 1, further comprising a step of:

simultaneously with step (d), exposing the immersed component to a flux of zirconium atoms.

3. The process of claim wherein:

step (b) comprises heating the metallic femoral component at a temperature between about 100° C. and 1000° C. for at least 10 minutes.

4. The process of claim 1, wherein the partial pressure of said oxygen-containing gas is in a range from $5 \times 10^{-6}$ to $1 \times 10^{-3}$ Torr.

5. A metal femoral component produced by the process of claim 1.

6. The process of claim 1 wherein the adhesion coating is selected from the group consisting of platinum, iridium and a platinum-iridium alloy.

* * * * *